United States Patent [19]

Carlson et al.

[11] Patent Number: 4,677,240

[45] Date of Patent: Jun. 30, 1987

[54] HYDROCARBON CONVERSION PROCESSES OVER CRYSTALLINE BOROSILICATE CATALYSTS FOR PSEUDOCUMENE RECOVERY

[75] Inventors: Ronald E. Carlson; Stephen R. Ely, both of Naperville; Allen I. Feinstein, Wheaton; Ibrahim Ghanayem, Downers Grove, all of Ill.

[73] Assignee: Amoco Corporation, Chicago, Ill.

[21] Appl. No.: 817,817

[22] Filed: Jan. 10, 1986

[51] Int. Cl.$^4$ .......................... C07C 4/12; C07C 5/22
[52] U.S. Cl. ..................................... 585/488; 585/474
[58] Field of Search ............................. 585/474, 488

[56] References Cited

U.S. PATENT DOCUMENTS

| | | | |
|---|---|---|---|
| 2,385,524 | 9/1945 | Mattox | 585/474 |
| 3,646,236 | 2/1972 | Keith et al. | 585/474 |
| 4,431,857 | 2/1984 | Feinstein | 585/488 |

*Primary Examiner*—Curtis R. Davis
*Attorney, Agent, or Firm*—Frederick S. Jerome; William H. Magidson; Ralph C. Medhurst

[57] ABSTRACT

A catalytic process is provided for upgrading a hydrocarbon feed stream containing pseudocumene together with a fraction of close boiling hydrocarbon compounds having a normal boiling point in a temperature range of about 320° F. to about 365° F. comprising contacting such hydrocarbon feed steam in the presence of hydrogen with a catalyst comprising AMS-1B crystalline borosilicate molecular sieve whereby such close boiling hydrocarbon compounds are converted to compounds having a normal boiling point below a temperature of about 300° F., and fractionating the effluent product stream.

16 Claims, No Drawings

HYDROCARBON CONVERSION PROCESSES OVER CRYSTALLINE BOROSILICATE CATALYSTS FOR PSEUDOCUMENE RECOVERY

BACKGROUND OF THE INVENTION

This invention relates to a catalytic process for upgrading a hydrocarbon feed containing alkyl-substituted aromatic compounds, paraffins, and naphthenes using a catalyst formed from crystalline borosilicate AMS-1B and more particularly relates to a method of selectively hydrodealkylating aromatic compounds while converting paraffins and naphthenes whereby a desired product mix is obtained and especially relates to a method to recover pseudocumene from a mixture of close-boiling hydrocarbons.

Several polymethylbenzenes are important intermediate products in the chemical industry. Particular di-, tri-, and tetra-methylbenzenes are oxidized to produce polycarboxylic acids and anhydrides of aromatic acids which are useful in the manufacture of synthetic fibers and plastics. Recent interest in manufacturing anhydrides of the most important aromatic tri-carboxylic acids, trimellitic (1,2,4-benzene-tricarboxylic acid) is due to its use in trimellitic ester plasticizers. The commercial method of producing trimellitic anhydride is by oxidation of pseudocumene (1,2,4-trimethylbenzene).

Pseudocumene, which as a purified raw material constitutes the largest single item of cost in the manufacture of the anhydride, is recovered by super fractionation of existing streams. Such a process, as will be realized, has involved high operation costs and has limited yield.

Fractionation of a mixed aromatics stream such as an extracted, heavy catalytic reformate is suitable to recover purified pseudocumene provided nonaromatics are absent. The close fractionation necessary is done in two fractionators (each containing about 100 trays) which remove, successively, aromatics boiling above and below pseudocumene. Typically, the fractionation feed of $C_9$ aromatics from reformates contain only about 40 percent pseudocumene. Such low pseudocumene content requires relatively large fractionation towers.

Purity of a pseudocumene feed for oxidation to produce trimellitic anhydride is critical. The presence of other alkyl-substituted aromatic compounds has a detrimental effect on both the yield and purity of trimellitic anhydride. Furthermore, some aromatic impurities undergo oxidation to compounds which inhibit the oxidation of pseudocumene to trimellitic anhydride.

Presence of nonaromatic hydrocarbons and naphthenes in a mixed aromatics stream can make recovery of purified pseudocumene by fractionation economically unattractive or even impossible. As the paraffin concentration in purified pseudocumene approaches 2 wt. % or more, the oxygen consumed in oxidizing the paraffins represents a significant penalty in production costs for a trimellitic anhydride process. For example, a heavy catalytic reformate contains a low concentration of pseudocumene together with significant amounts of paraffins which have normal boiling point temperatures near the normal boiling point temperature of pseudocumene (about 337° F.). Recovery of pseudocumene having a desired purity by fractionation of such a reformate is very difficult or impossible without a pretreatment process.

U.S. Pat. Nos. 4,268,420; 4,269,813; 4,285,919; 4,292,457; 4,292,458; and 4,327,236, all incorporated by reference herein, disclose uses of crystalline borosilicate AMS-1B in a catalyst for various hydrocarbon conversion processes. These processes include hydrocracking, hydrodealkylation, disproportionation of aromatics, isomerization of normal paraffins and naphthenes, and especially the isomerization of alkylaromatics, such as xylenes. Crystalline borosilicate AMS-1B formulated as a catalyst including an alumina matrix material and a catalytically-active metal such as molybdenum simultaneously can isomerize xylenes and predominantly convert ethylbenzene through hydrodeethylation.

The process of this invention provides a method to convert alkyl-substituted aromatic compounds by selective hydrodealkylation of ethyl, propyl, and butyl groups. Because of the difficulty of removing some paraffins and naphthenes from pseudocumene by distillation due to closeness of boiling points and nonideal behavior of such mixtures, it is desirable to convert paraffins and naphthenes to other hydrocarbon species by hydrocracking or isomerization. A process which permits a single catalyst composition simultaneously to convert paraffins and naphthenes and selectively hydrodealkylate aromatic compounds would be useful. A process which permits both without having any significant effect on the pseudocumene in the feed would be very advantageous.

SUMMARY OF THE INVENTION

A source of pseudocumene (1,2,4-trimethylbenzene) is upgraded by contacting a feed containing pseudocumene and a fraction of close boiling hydrocarbon compounds which have a normal boiling point in a temperature range of about 320° F. to about 365° F. under hydrodealkylation conditions and in the presence of hydrogen with a catalyst comprising AMS-1B crystalline borosilicate. The close boiling hydrocarbon compounds are converted to compounds having a normal boiling point below about 300° F. without a substantial change of the weight percent pseudocumene content in the resulting stream. Thus, the resulting stream is more easily separated by fractional distillation to recover a stream containing 90 wt % or more of pseudocumene.

BRIEF DESCRIPTION OF THE INVENTION

This invention is a method to upgrade a hydrocarbon feed, especially a feed containing pseudocumene, other monocyclic aromatic hydrocarbons, paraffins, and naphthenes which have normal boiling points above about 320° F.

More particularly, this invention is a catalytic process using an AMS-1B crystalline borosilicate-based catalyst system for selective conversion of undesirable compounds in a hydrocarbon feed that are difficult to separate from pseudocumene by fractionation due to closeness of boiling points and nonideal behavior of hydrocarbon mixtures. In this invention a borosilicate-based catalyst selectively hydrodealkylates ethyl, propyl, and butyl groups while it hydrocracks paraffins and naphthenes without having any significant effect on the pseudocumene in the feed. Thus, in the resulting product the amount of pseudocumene is increased relative to other hydrocarbon compounds which have a normal boiling point in a temperature range of about 320° F. to about 365° F. The normal boiling points of selected hydrocarbons are given in Table I.

TABLE I

| Compound | Boiling Point, °F. |
| --- | --- |
| Benzene | 176.0 |
| Toluene | 231.0 |
| Ethylbenzene | 277.2 |
| Isopropylbenzene | 305.6 |
| n-Propylbenzene | 319.1 |
| 1-Ethyl-3-methylbenzene | 322.3 |
| 1-Ethyl-4-methylbenzene | 323.6 |
| 1,3,5-Trimethylbenzene | 328.5 |
| 1-Ethyl-2-methylbenzene | 329.4 |
| Isopropenylbenzene | 329.7 |
| Tert-butylbenzene | 334.4 |
| 1,2,4-Trimethylbenzene | 336.8 |
| Tert-butyl-cyclohexane | 340.7 |
| Isobutylbenzene | 343.0 |
| Decane | 345.4 |
| 1-Isopropyl-3-methylbenzene | 347.3 |
| 1,2,3-Trimethylbenzene | 349.0 |
| 1-Isopropyl-4-methylbenzene | 350.8 |
| 1-Isopropyl-2-methylbenzene | 352.7 |
| Sec-butyl-cyclohexane | 354.8 |
| n-Butylbenzene | 356.0 |
| n-Butyl-cyclohexane | 357.7 |
| 1,3-Diethylbenzene | 357.8 |
| 1,2-Diethylbenzene | 362.1 |
| 1,3-Dimethyl-5-ethyl-benzene | 362.7 |
| 1,4-Diethylbenzene | 362.8 |
| 1,4-Dimethyl-2-ethyl-benzene | 370.2 |
| 1,4-Dimethyl-1-ethyl-benzene | 371.1 |
| 1,2-Dimethyl-4-ethyl-benzene | 373.6 |
| 1,2,4,5-Tetramethylbenzene | 386.2 |

Hydrocarbon streams which can be converted using the process of this invention may include alkyl mono and polycyclic aromatic hydrocarbons containing side chains of 2 to about 12 carbon atoms. The preferable feed useful in this invention comprises pseudocumene and mixtures of monocyclic aromatic hydrocarbons, paraffins, and naphthenes.

Aromatic hydrocarbons have chemical structures related to benzene, i.e., a compound consisting of six carbon atoms in a ring with one hydrogen on each carbon. Paraffins (alkanes and cycloalkanes) are a series of hydrocarbon compounds whose formulas differ by an integral number of $CH_2$-groups. The first compound in the paraffin series is methane ($C_1$) with one carbon atom. Paraffins with more than three carbon atoms have more than one chemical structure. These different structures with the same number of carbons are known as isomers, i.e., normal butane and isobutane are $C_4$ isomers. There are 75 isomers of $C_{10}$ paraffins. Naphthenes have chemical structures consisting of three or more carbon atoms arranged in the form of rings with two hydrogen on each carbon.

A pseudocumene containing hydrocarbon feed stream which can be upgraded according to this invention contains at least about 1 wt % pseudocumene, preferably more than about 2 wt %. A typical feed stream also contains $C_{10}$ paraffins and naphthenes and various alkyl benzenes which would be difficult to separate from pseudocumene by distillation. Such difficult to separate hydrocarbons typically have a normal boiling point of about 300° F. to about 370° F. When a distillation fraction containing more than 90 wt % pseudocumene is desired, distillation feed content of hydrocarbons which have a normal boiling point of about 320° F. to about 365° F. is critical. Alkyl benzenes which are difficult to separate from pseudocumene include propylbenzenes, butylbenzenes, ethyltoluenes and diethylbenzenes. Of these, butylbenzenes are the most difficult to separate while diethylbenzenes are the least difficult. Thus, an advantageous process according to this invention especially would remove butylbenzenes.

A useful feed stream contains about 0.01 to 5 wt % $C_{10}$ paraffins and naphthenes, about 0.1 to about 30 wt % propyl and butylbenzenes, and about 0.5 to 70 wt % ethyltoluenes (also may include about 0.01 to about 20 wt % diethylbenzenes). A typical feed stream contains about 0.05 to about 3 wt % $C_{10}$ paraffins and naphthenes, about 0.2 to about 20 wt % propyl and butylbenzenes, and about 1 to 50 wt % ethyltoluenes.

Monocyclic aromatic hydrocarbons, or mixtures thereof, used in the process of this invention can be converted in the presence of other substances such as other hydrocarbon-based molecules. Thus, a feed used in the process of this invention comprising a monocyclic aromatic hydrocarbon also can contain other hydrocarbons such as alkanes, alkenes, methane, hydrogen, and inert gases. A process in which partially reacted hydrocarbons are recycled will contain a mixture including alkanes, alkenes, methane, and aromatics. Typically, a hydrocarbon feed used in this invention contains about 2 to 80 wt. % pseudocumene and preferably contains 5 to 80 wt. % pseudocumene. Petroleum hydrocarbon distillates, and the like, containing at least a significant (about 2%) content of pseudocumene are satisfactory feeds for the present process. A typical feed is a heavy cut from petroleum reformates in which a very high proportion of the alkyl carbon atom content is contained as the alkyl substituents on aromatic rings. The alkyl substituents in a typical reformate are to a major extent, methyl groups, with some ethyl groups present together with a few propyl and butyl groups. Longer alkyl chains are present in such a small amount that they can be disregarded.

In accordance with the process of this invention, a heavy reformate is subjected to hydrodealkylation in the presence of hydrogen with a catalyst comprising AMS-1B crystalline borosilicate under the above described conditions.

In the practice of the process of the invention, broad ranges of reaction conditions including the reaction conditions conventionally employed in hydrocracking can be employed. Usually, however, a reaction temperature is in a range of from about 500° F. to about 1200° F., preferably about 600° F. to about 1000° F.; a reaction pressure is in a range of from about 20 to about 800 pounds per square inch gage (psig), preferably about 50 to about 400 psig; a mole ratio of hydrogen to feed hydrocarbon is in a range of from about 1:1 to about 50:1, preferably about 2:1 to about 20:1; a weight hourly space velocity (WHSV) is in a range of from about 0.1 to about 100 per hour ($hr^{-1}$), preferably about 0.5 to about 20 $hr^{-1}$, and hydrogen having a purity of at least 75 mol % is used.

In a preferred embodiment of this invention, a hydrocarbon feed stream containing pseudocumene, other alkyl aromatics, naphthenes, and paraffins is treated with a catalyst composition comprising an AMS-1B crystalline borosilicate in the presence of hydrogen at a reaction temperature in a range of from about 750° F. to about 850° F., a reaction pressure in a range of from about 100 to about 300 psig, a mole ratio of hydrogen to feed hydrocarbon in a range of from about 3:1 to about 10:1, and a WHSV in a range of from about 2 to about 10 $hr^{-1}$, The preferable hydrocarbon conversion process of this invention is a process to hydrodealkylate a mixture of aromatic hydrocarbons while converting paraffins and naphthenes to other hydrocarbon products which have lower boiling points than their precursors. In such a process a mixture containing polymethylbenzenes, usually deficient in pseudocumene, other monocyclic alkyl aromatics, paraffins, and naphthenes is contacted with a catalyst composition such as one based on the crystalline borosilicate AMS-1B incorporated in a matrix material and impregnated with a molybdenum compound. This catalyst composition hydrodealkylates aromatic hydrocarbons selectively of ethyl, propyl, and butyl groups to increase the polymethylbenzene fraction of the alkyl-substituted aromatic compounds in the hydrocarbon mixture. Simultaneous with the hydrodealkylation of ethyl, propyl, and butyl benzenes, paraffin and naphthenes are converted to lower boiling hydrocarbon products which are easily separated from a pseudocumene rich fraction as by distillation.

In the process of this invention a hydrocarbon stream containing pseudocumene, other alkyl aromatics, naphthenes, and paraffins is treated with a catalyst composition comprising an AMS-1B crystalline borosilicate such that at least 30 wt % of the $C_{10}$ paraffins and naphthenes are converted to $C_1$-$C_7$ paraffins, at least 80 wt % of propyl and butylbenzenes are converted to benzene and low boiling hydrocarbons such as alkanes, and at least 20 wt % of ethyltoluenes are converted to toluene. Preferably, according to this invention, at least 50 wt % of $C_{10}$ paraffins and naphthenes, at least 90 wt % of propyl and butylbenzenes and at least 50 wt % of ethyltoluenes are so converted.

In a preferred embodiment of this invention, a hydrocarbon feed stream containing pseudocumene, other alkyl aromatics, naphthenes and paraffins is treated with a catalyst composition comprising an AMS-1B crystalline borosilicate such that at least 75 wt % of the $C_{10}$ paraffins and naphthenes are converted to $C_1$-$C_7$ paraffins, at least 95 wt % of propyl and butylbenzenes are converted to benzene and low boiling hydrocarbons such as alkanes, and at least 75 wt % of ethyltoluenes are converted to toluene.

Pseudocumene content after treatment according to this invention is not changed substantially. In this regard, no substantial change means that the weight percent (wt %) of pseudocumene in the starting feed stream is within about 10% of the amount in the treated stream.

The resulting hydrocarbon stream after treatment may be posttreated by conventional distillation techniques to produce a concentrated (typically about 95 to 99 wt %) pseudocumene stream, preferably at least 97 wt %.

The catalyst useful in this invention is based on the crystalline borosilicate molecular sieve, AMS-1B, described in U.S. Pat. Nos. 4,268,420; 4,269,813; 4,285,919; 4,292,457; 4,292,458; and 4,327,236 incorporated herein by reference. A particularly useful catalyst for this invention contains AMS-1B in which a metal is incorporated by ion exchange, impregnation, or other means.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

0.9±0.2 $M_{2/n}O:B_2O_3:ySiO_2:zH_2O$ wherein M is at least one cation, n is the valence of the cation, y is between 4 and about 600 and z is between 0 and about 160.

TABLE II

| d-Spacing Å (1) | Assigned Strength (2) |
|---|---|
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M | notes:
(1) Copper K alpha radiation.
(2) VS = very weak; W - weak; M = medium; MS = medium strong, VS = very strong.

The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

| | Broad | Preferred | Most Preferred |
|---|---|---|---|
| $SiO_2/B_2O_3$ | 5-400 | 10-150 | 10-80 |
| $R_2O^+/[R_2O^+ + M_{2/n}O]$ | 0.1-1.0 | 0.2-0.97 | 0.3-0.97 |
| $OH^-/SiO_2$ | 0.1-11 | 0.1-2 | 0.1-1 |
| $H_2O/OH^-$ | 10-4000 | 10-500 | 10-500 | wherein R is an organic compound and M is at least one cation having a valence n, such as an alkali metal or an alkaline earth metal cation. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring blender. After the pH is checked and adjusted, if necessary, the resulting slurry is transferred to a closed crystallization vessel for a suitable time. After crystallization, the resulting crystalline produce can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates and Ludox, a stabilized polymer of silicic acid manufactured by E. I. DuPont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium, and magnesium. Ammonium cations may be used alone or in conjunction with such metal cations. Since basic conditions are required for crystallization of the molecular sieve of this invention, the source of such a cation usually is a hydroxide such as sodium hydroxide. Alternatively, AMS-1B can be prepared directly in the hydrogen form by replacing such metal cation hydroxides with an organic base such as ethylene diamine.

Organic templates useful in preparing AMS-1B crystalline borosilicate include alkylammonium cations or precursors thereof such as tetraalkylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_2BO_3$) are dissolved in distilled or deionized water followed by addition of the organic template. The pH may be adjusted between about $11.0 \pm 0.2$ using a compatible acid or base such as sodium bisulfate or sodium hydroxide. After sufficient quantities of silicic acid polymer (Ludox) are added with intensive mixing, preferably the pH is again checked and adjusted to a range of about $11.0 \pm 0.2$. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about one to about seven days, at a temperature ranging from about 212° to about 480° F., preferably from about 260° to about 390° F. The crystallizing material can be stirred or agitated as in a rocker bomb. Preferably, the crystallization temperature is maintained below the decomposition temperature of the organic template compound. Especially preferred conditions are crystallizing at about 330° F. for about five to about seven days. Samples of material can be removed during crystallization to check the degree of crystallization and determine the optimum crystallization time.

The crystalline material formed can be separated and recovered by well-known means such as filtration with washing. This material can be mildly dried for anywhere from a few hours to a few days at varying temperatures, typically from about 80° F. to about 390° F., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 500° F. to about 1560° F. and preferably from about 840° F. to 1100° F. Extreme calcination temperatures or prolonged crystallization times may prove detrimental to the crystal structure or may totally destroy it. Generally there is no need to raise the calcination temperature beyond about 1100° F. in order to remove organic material from the originally formed crystalline material. Typically, the molecular sieve material is dried in a forced draft oven at 165° C. for about 16 hours and is then calcined in air in a manner such that the temperature rise does not exceed 225° F. per hour until a temperature of about 1000° F. is reached. Calcination at this temperature usually is continued for about 4 to 16 hours.

A catalytically active material can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The original cation in the AMS-1B crystalline borosilicate, which usually is sodium ion, can be replaced all or in part by ion exchange with other cations including other metal ions and their amine complexes, alkylammonium ions, ammonium ions, hydrogen ions, and mixtures thereof. Preferred replacing cations are those which render the crystalline borosilicate catalytically active, especially for hydrocarbon conversion. Typical catalytically active ions include hydrogen, metal ions of Groups IB, IIA, IIB, IIIA, VB, VIB and VIII, and of manganese, vanadium, chromium, uranium, and rare earth elements.

Also, water soluble salts of catalytically active materials can be impregnated onto the crystalline borosilicate of this invention. Such catalytically active materials include metals of Groups IB, IIA, IIB, IIIA, IIIB, IVB, VB, VIB, VIIB, and VIII, and rare earth elements.

Catalyst compositions useful in this invention preferably contain hydrogen-form AMS-1B crystalline borosilicate molecular sieve.

In addition, preferable catalyst compositions are prepared containing Groups VIB and VIII elements while most preferable Groups VIB and VIII elements have atomic numbers below 46. Such catalytically active metals include molybdenum, ruthenium, rhodium, chromium, iron, cobalt, and nickel; molybdenum is preferable. Mixtures of Group VIII elements can be used.

Furthermore, preferable catalyst compositions are prepared containing a metal of Groups VIB and VIII in combination with another metal ion or compound including Groups IB, IIB, IIIB, IVB, VB, VIB, VIIB, and VIII metals and rare earth elements. Specific additional catalytic materials include ions and compounds of lanthanum, molybdenum, tungsten, and nobel metals. Such nobel metals include ruthenium, osmium, rhodium, iridium, palladium, and platinum. Other additional catalytic materials can be ions and compounds of scandium, yttrium, titanium, zirconium, hafnium, vanadium, niobium, tantalum, chromium, cerium, manganese, iron, zinc, and cadmium. Specific combinations of nonnoble metals of Group VIII and other catalytic materials include ions of compounds of nickel and osmium, nickel and lanthanum, nickel and palladium, nickel and iridium, nickel and molybdenum, and nickel and tungsten.

Ion exchange and impregnation techniques are well-known in the art. Typically, an aqueous solution of a cationic species is exchanged one or more times at about 80° to about 212° F. A hydrocarbon-soluble metal compound such as a metal carbonyl also can be used to place a catalytically active material. Impregnation of a catalytically active compound on the borosilicate or on a composition comprising the crystalline borosilicate suspended in and distributed throughout a matrix of a support material, such as a porous refractory inorganic oxide such as alumina, often results in a suitable catalytic composition. A combination of ion exchange and impregnation can be used. Presence of sodium ion in a composition usually is detrimental to catalytic activity.

The amount of catalytically active material placed on the AMS-1B borosilicate can vary from about 0.01 wt. % to about 30 wt. %, typically from about 0.05 wt % to about 25 wt. %, depending on the process use intended. The optimum amount can be determined easily by routine experimentation.

The AMS-1B crystalline borosilicate useful in this invention may be used as pure material in a catalyst or may be admixed with or incorporated within various binders or matrix materials depending upon the intended process use. The crystalline borosilicate can be combined with active or inactive materials, synthetic or naturally-occurring zeolites, as well as inorganic or organic materials which would be useful for binding the borosilicate. Well-known materials include silica, silica-alumina, alumina, magnesia, titania, zirconia, alumina sols, hydrated aluminas, clays such as bentonite or kaolin, or other binders well-known in the art. Typically, the borosilicate is incorporated within a matrix material by blending with a sol of the matrix material and gelling the resulting mixture. Also, solid particles of the borosilicate and matrix material can be physically admixed. Typically, such borosilicate compositions can be pelletized or extruded into useful shapes. The crystalline borosilicate content can vary anywhere from a few up to 100 wt. % of the total composition. Catalytic compositions can contain about 0.1 wt. % to about 100 wt. % crystalline borosilicate material and preferably contain about 20 wt. % to about 95 wt. % of such material and most preferably contain about 20 wt. % to about 80 wt. % of such material.

Catalytic compositions comprising the crystalline borosilicate material of this invention and a suitable matrix material can be formed by adding a finely-divided crystalline borosilicate and a catalytically active metal compound to an aqueous sol or gel of the matrix material. The resulting mixture is thoroughly blended and gelled, typically by adding a material such as ammonium hydroxide. The resulting gel can be dried and calcined to form a composition in which the crystalline borosilicate and catalytically active metal compound are distributed throughout the matrix material.

Specific details of catalyst preparations are described in U.S. Pat. No. 4,269,813 and European Published Application No. 68,796 both incorporated by reference herein.

This invention is demonstrated but not limited by the following examples.

EXAMPLE 1

A crystalline borosilicate-based catalyst was prepared in a manner similar to that described in U.S. Pat. No. 4,269,813 and contained a molybdenum-impregnated AMS-1B crystalline borosilicate incorporated within an alumina binder. The total catalyst composition contained 80 wt. % alumina and 3 wt. % molybdenum. The AMS-1B crystalline borosilicate contained 0.5 wt. % boron and exhibited an X-ray diffraction spectrum similar to that described in Table II.

Six grams of the extruded and activated catalyst were placed in a ½-inch tubular stainless steel reactor and heated to 850° F. under $H_2$ pressure of about 200 psig. The catalyst was treated with hydrogen for 2 hours before hydrocarbon feed was started. Heavy reformate was passed through the tubular reactor under the following conditions:

| | |
|---|---|
| Temperature | 850° F. |
| Pressure | 200 psig |
| WHSV | 4.3 hr$^{-1}$ |
| $H_2$/HC, mole ratio | 5.0 |

The reactor effluent stream was sampled for analysis after cooling to ambient temperature and reducing pressure to about 3 psig.

The hydrocarbon composition of the total reactor effluent stream for this operation is shown below. The composition of the heavy reformate feed stream is also in Table III. These data show that a substantial amount of the undesirable components that boil close to pseudocumene are converted to lower boiling, easily separable, components without having any detrimental effect to pseudocumene. Specifically, by reacting heavy reformate over the borosilicate-based catalyst at 850° F., 200 psig pressure with a hydrogen to hydrocarbon ($H_2$/HC) mole ratio of 5/1 at a weight hourly space velocity (WHSV) of 4.3 hr$^{-1}$, we have simultaneously converted about 82% of the $C_{10}$ paraffins/naphthenes to $C_1$-$C_7$ paraffins, 100% of the propyl and butylbenzenes to benzene and 80% of the ethyltoluenes to toluene. The pseudocumene content of the total reactor effluent was 21% as compared to 22% in the heavy reformate feed.

In this example, the ratio of pseudocumene to $C_9$ aromatics plus butylbenzenes has increased from 34% to 59%. The process produced a stream which may be easily fractionated as by conventional distillation to obtain a high purity pseudocumene concentrate.

TABLE III

| Reactor Effluent Liquid Hydrocarbon Composition (Wt. %) | | |
|---|---|---|
| | Feed | Ex. 1 |
| Components, wt. % | | |
| $C_1$-$C_7$ Paraffins/Naphthenes | — | 15.71 |
| $C_{10}$ Paraffins/Naphthenes | 1.63 | 0.30 |
| Benzene | — | 4.91 |
| Toluene | — | 20.04 |
| Ethylbenzene | — | 0.90 |
| Xylenes | — | 7.57 |
| Propylbenzenes | 4.85 | 0.01 |
| Ethyltoluenes | 24.18 | 3.33 |
| Trimethylbenzenes | 34.61 | 32.55 |
| Pseudocumene | 22.10 | 21.16 |
| Butylbenzenes | 1.33 | — |
| Diethylbenzenes | 6.89 | 0.13 |
| Dimethylethylbenzenes | 12.42 | 1.71 |
| $C_{10}$+ Aromatics | 14.09 | 12.86 |
| Conversions, Wt. % | | |
| Butylbenzenes | | 100 |
| Propylbenzenes | | 99.98 |
| Ethyltoluenes | | 86.23 |
| $C_{10}$ Paraffins/Naphthenes | | 81.60 |

EXAMPLES 2 and 3

The effect of WHSV at a temperature of 850° F. was demonstrated by repeating Example 1 at a hydrogen to hydrocarbon mole ratio of 6.2. The hydrocarbon composition of the total reactor effluent stream for these examples is shown in Table IV.

TABLE IV
TREATMENT OF HEAVY REFORMATE OVER THE BOROSILICATE-BASED CATALYST

| | Feed Composition | EXAMPLE 2 | EXAMPLE 3 |
|---|---|---|---|
| WHSV, hr$^{-1}$ | | 12.38 | 6.46 |
| | | Yield Wt. % | Wt. % |
| Components, wt. % | | | |
| $C_1$-$C_7$ Paraffins/Naphthenes | — | 11.48 | 14.03 |
| $C_{10}$ Paraffins/Naphthenes | 1.63 | 0.67 | 0.43 |
| Benzene | | 4.57 | 4.76 |
| Toluene | | 15.15 | 18.15 |
| Ethylbenzene | | 1.37 | 1.25 |
| Xylenes | | 4.92 | 6.24 |
| Propylbenzenes | 4.85 | 0.20 | 0.04 |
| Ethyltoluenes | 24.18 | 10.38 | 6.23 |
| Trimethylbenzenes | 34.61 | 32.69 | 32.37 |
| Pseudocumene | 22.10 | 21.25 | 21.06 |
| Butylbenzenes | 1.33 | — | — |
| Diethylbenzenes | 6.89 | 0.80 | 0.32 |
| Dimethylethylbenzenes | 12.42 | 2.67 | 2.21 |
| $C_{10}$+Aromatics | 14.09 | 15.10 | 13.96 |
| Conversions, Wt. % | | | |
| Butylbenzenes | | 100 | 100 |
| Propylbenzenes | | 95.88 | 99.17 |
| Ethyltoluenes | | 57.07 | 74.24 |
| $C_{10}$ Paraffins/Naphthenes | | 58.90 | 73.61 |

EXAMPLES 4–7

Example 1 was repeated except at a temperature of 800° F. and several operating conditions as shown in Table V.

EXAMPLES 8–12

Example 1 was repeated except at a temperature of 750° F. and several operating conditions as shown in Table VI.

EXAMPLE 13

Example 1 was repeated except at a temperature of 700° F. and several operating conditions as shown in Table VII.

TABLE V
TREATMENT OF HEAVY REFORMATE OVER THE BOROSILICATE-BASED CATALYST AT 800° F.

| | EXAMPLE 4 | 5 | 6 | 7 |
|---|---|---|---|---|
| Conditions | | | | |
| Temperature, °F. | 800 | 800 | 800 | 800 |
| Pressure, psig | 200 | 200 | 200 | 200 |
| $H_2$/HC Mole Ratio | 5.02 | 5.07 | 5.15 | 4.73 |
| WHSV, hr$^{-1}$ | 13.30 | 6.54 | 4.49 | 3.50 |
| Contact Time, Sec. | 2.12 | 4.29 | 6.17 | 8.50 |
| Components Yield, Wt. % | | | | |
| $C_1$-$C_7$ Paraffins/Naphthenes | 8.38 | 11.09 | 12.99 | 13.84 |
| $C_{10}$ Paraffins/Naphthenes | 0.92 | 0.76 | 0.57 | 0.52 |
| Benzene | 3.98 | 4.25 | 4.47 | 4.67 |
| Toluene | 11.15 | 14.85 | 17.19 | 18.81 |
| Ethylbenzene | 1.50 | 1.71 | 1.69 | 1.56 |
| Xylenes | 3.15 | 4.40 | 5.58 | 6.22 |
| Propylbenzenes | 0.56 | 0.12 | 0.04 | 0.02 |
| Ethyltoluenes | 15.73 | 11.03 | 8.07 | 6.28 |
| Trimethylbenzenes | 33.56 | 32.92 | 32.71 | 32.67 |
| Pseudocumene | 21.79 | 21.48 | 21.53 | 21.27 |
| Butylbenzenes | — | — | — | — |
| Diethylbenzenes | 1.48 | 0.70 | 0.40 | 0.27 |
| Dimethylethylbenzenes | 3.07 | 2.72 | 2.33 | 2.06 |
| $C_{10}$+ Aromatics | 16.51 | 15.45 | 13.96 | 13.08 |
| Conversions, Wt. % | | | | |
| Butylbenzenes | 100 | 100 | 100 | 100 |
| Propylbenzenes | 88.45 | 97.53 | 99.18 | 99.59 |
| Ethyltoluenes | 34.95 | 54.38 | 66.63 | 74.03 |
| $C_{10}$ Paraffins/Naphthenes | 43.56 | 53.37 | 65.03 | 68.10 |

TABLE VI
TREATMENT OF HEAVY REFORMATE OVER THE BOROSILICATE-BASED CATALYST AT 750° F.

| | EXAMPLE 8 | 9 | 10 | 11 | 12 |
|---|---|---|---|---|---|
| Conditions | | | | | |
| Temperature, °F. | 750 | 750 | 750 | 750 | 750 |
| Pressure, psig | 200 | 200 | 200 | 200 | 200 |
| $H_2$/HC Mole Ratio | 4.93 | 4.95 | 5.10 | 5.14 | 4.94 |
| WHSV, hr$^{-1}$ | 15.95 | 7.86 | 5.33 | 3.95 | 3.34 |
| Contact Time, Sec. | 2.05 | 4.15 | 5.97 | 8.00 | 9.77 |
| Components Yield, Wt. % | | | | | |
| $C_1$-$C_7$ Paraffins/Naphthenes | 7.23 | 9.46 | 10.17 | 11.67 | 12.18 |
| $C_{10}$ Paraffins/Naphthenes | 1.02 | 1.00 | 0.81 | 0.65 | 0.72 |
| Benzene | 3.43 | 3.97 | 4.21 | 4.02 | 4.22 |
| Toluene | 8.26 | 12.14 | 14.20 | 15.21 | 16.42 |
| Ethylbenzene | 1.36 | 1.91 | 2.08 | 2.13 | 2.16 |
| Xylenes | 2.31 | 3.89 | 4.57 | 5.30 | 5.76 |
| Propylbenzenes | 0.94 | 0.19 | 0.07 | 0.03 | 0.02 |
| Ethyltoluenes | 18.97 | 14.86 | 12.78 | 10.70 | 9.55 |
| Trimethylbenzenes | 33.88 | 33.12 | 33.04 | 32.95 | 32.65 |
| Pseudocumene | 21.96 | 21.61 | 21.59 | 21.48 | 21.29 |
| Butylbenzenes | 0.02 | — | — | — | — |
| Diethylbenzenes | 1.97 | 1.03 | 0.75 | 0.56 | 0.47 |
| Dimethylethylbenzenes | 3.23 | 2.92 | 2.65 | 2.45 | 2.22 |
| $C_{10}$+ Aromatics | 17.36 | 15.51 | 14.66 | 14.33 | 13.63 |
| Conversions, Wt. % | | | | | |
| Butylbenzenes | 98.50 | 100 | 100 | 100 | 100 |
| Propylbenzenes | 80.62 | 96.08 | 98.55 | 99.38 | 99.59 |
| Ethyltoluenes | 21.55 | 38.54 | 47.15 | 55.75 | 60.50 |
| $C_{10}$ Paraffins/Naphthenes | 37.42 | 38.65 | 50.31 | 60.12 | 55.83 |

TABLE VII
TREATMENT OF HEAVY REFORMATE OVER THE BOROSILICATE-BASED CATALYST AT 700° F.

| | EXAMPLE 13 | 14 | 15 |
|---|---|---|---|
| Conditions | | | |
| Temperature, °F. | 700 | 700 | 700 |
| Pressure, psig | 200 | 200 | 200 |
| $H_2$/HC Mole Ratio | 4.99 | 4.99 | 5.17 |
| WHSV, hr$^{-1}$ | 4.96 | 3.12 | 2.52 |
| Contact Time, Sec. | 6.25 | 9.93 | 11.96 |
| Components Yield, Wt. % | | | |
| $C_1$-$C_7$ Paraffins/Naphthenes | 7.34 | 9.41 | 9.55 |
| $C_{10}$ Paraffins/Naphthenes | 1.36 | 1.12 | 0.91 |
| Benzene | 3.52 | 3.67 | 3.65 |
| Toluene | 9.22 | 11.39 | 12.22 |
| Ethylbenzene | 1.80 | 2.18 | 2.30 |
| Xylenes | 3.10 | 4.17 | 4.62 |
| Propylbenzenes | 0.41 | 0.11 | 0.06 |
| Ethyltoluenes | 18.45 | 15.73 | 14.81 |
| Trimethylbenzenes | 33.67 | 33.14 | 33.32 |
| Pseudocumene | 21.98 | 21.70 | 21.82 |
| Butylbenzenes | — | — | — |
| Diethylbenzenes | 1.51 | 1.06 | 0.93 |
| Dimethylethylbenzenes | 3.22 | 2.90 | 2.75 |
| $C_{10}$ Aromatics | 16.40 | 15.08 | 14.88 |
| Conversions, Wt. % | | | |

TABLE VII-continued

TREATMENT OF HEAVY REFORMATE OVER
THE BOROSILICATE-BASED CATALYST AT 700° F.

| | EXAMPLE | | |
|---|---|---|---|
| | 13 | 14 | 15 |
| Butylbenzenes | 100 | 100 | 100 |
| Propylbenzenes | 91.55 | 97.73 | 98.76 |
| Ethyltoluenes | 23.70 | 34.95 | 38.75 |
| $C_{10}$ Paraffins/Naphthenes | 16.56 | 31.28 | 44.17 |

We claim:

1. A process to upgrade a hydrocarbon feed stream containing at least 2 wt % pseudocumene together with about 0.01 to about 5 wt % $C_{10}$ paraffins and naphthenes, about 0.1 to about 30 wt % propyl and butylbenzenes, and about 0.5 to about 70 wt % ethyltoluenes comprising contacting such hydrocarbon feed stream with a catalyst comprising AMS-1B crystalline borosilicate molecular sieve in the presence of hydrogen whereby at least 30 wt % of such $C_{10}$ paraffins and naphthenes are converted to $C_1$–$C_7$ paraffin and naphthenes, at least 80 wt % of such propyl and butylbenzenes are converted to benzene, and at least 20 wt % of such ethyltoluenes are converted to toluene and wherein the weight percent pseudocumene content of the resulting stream is not changed substantially.

2. The process of claim 1 wherein the hydrocarbon feed stream is contacted with the catalyst at temperature in a range of about 500° F. to 1200° F., a pressure in a range of about 20 to 800 psig, and a WHSV in a range of about 0.1 to 50 $hr^{-1}$.

3. The process of claim 1 wherein the hydrogen to hydrocarbon molar ratio is in a range of about 1:1 to 50:1.

4. The process of claim 1 wherein the feed stream is contacted with the catalyst and hydrogen with a hydrogen-to-hydrocarbon molar ratio in a range of about 2:1 to 20:1 at a temperature in a range of about 600° F. to 1000° F., a pressure in a range of about 50 to 400 psig, and a WHSV in a range of about 0.5 to 20 $hr^{-1}$.

5. The process of claim 1 wherein at least 50 wt % of the $C_{10}$ paraffins and naphthenes, at least 90 wt % of the propyl and butylbenzenes, and at least 50 wt % of the ethyltoluenes are converted.

6. The process of claim 1 wherein molybdenum is placed onto the AMS-1B crystalline borosilicate-based catalyst.

7. The process of claim 1 wherein the AMS-1B crystalline borosilicate is incorporated in an alumina, silica, or silica-alumina matrix.

8. The process of claim 1 wherein the AMS-1B crystalline borosilicate is incorporated in an alumina or silica-alumina matrix.

9. A process to upgrade a hydrocarbon feed stream containing about 2 to 80 wt % pseudocumene together with about 0.05 to about 3 wt % $C_{10}$ paraffins and naphthenes, about 0.2 to about 20 wt % propyl and butylbenzenes, and about 1 to about 50 wt % ethyltoluenes comprising contacting such hydrocarbon feed stream with a AMS-1B crystalline borosilicate-based catalyst incorporated in an alumina or silica-alumina matrix in the presence of hydrogen whereby at least 30 wt % of such $C_{10}$ paraffins and naphthenes are converted to $C_1$–$C_7$ paraffin and naphthenes, at least 80 wt % of such propyl and butylbenzenes are converted to benzene, and at least 20 wt % of such ethyltoluenes are converted to toluene and wherein the weight percent pseudocumene content of the resulting stream is not changed substantially.

10. The process of claim 9 wherein molybdenum is placed onto the AMS-1B crystalline borosilicate-based catalyst.

11. The process of claim 9 wherein the hydrogen-to-hydrocarbon molar ratio is in a range of about 1:1 to 50:1.

12. The process of claim 9 wherein the feed stream is contacted with the catalyst and hydrogen with a hydrogen-to-hydrocarbon molar ratio in a range of about 2:1 to 20:1 at temperature in a range of about 600° F. to 1000° F., a pressure in a range of about 50 to 400 psig, and a WHSV in a range of about 0.5 to 20 $hr^{-1}$.

13. The process of claim 9 wherein at least 50 wt % of the $C_{10}$ paraffins and naphthenes, at least 90 wt % of the propyl and butylbenzenes, and at least 50 wt % of the ethyltoluenes are converted.

14. A process to recover pseudocumene from a feed mixture containing $C_{10}$ paraffins and naphthenes, propyl and butylbenzenes, and ethyltoluenes comprising (A) contacting such feed mixture with a catalyst comprising an AMS-1B crystalline borosilicate-based composition in the presence of hydrogen at temperature in a range of about 500° F. to 1200° F., a pressure in a range of about 20 to 800 psig, and a WHSV in a range of about 0.1 to 50 $hr^{-1}$ and at a hydrogen-to-hydrocarbon molar ratio in a range of about 1:1 to 50:1 whereby at least 30 wt % of such $C_{10}$ paraffins and naphthenes are converted to $C_1$–$C_7$ paraffin and naphthenes, at least 80 wt % of such propyl and butylbenzenes are converted to benzene, and at least 20 wt % of such ethyltoluenes are converted to toluene and wherein the weight percent pseudocumene content of the resulting stream is not changed substantially; and (B) fractional distilling the resulting stream to recover a stream containing at least 90 wt % pseudocumene.

15. The process of claim 14 wherein the feed mixture is contacted with the catalyst and hydrogen with a hydrogen-to-hydrocarbon molar ratio in a range of about 2:1 to 20:1 at a temperature in a range of about 600° F. to 1000° F., a pressure in a range of about 50 to 400 psig, and a WHSV in a range of about 0.5 to 20 $hr^{-1}$.

16. The process of claim 15 wherein a stream is recovered containing at least 95 wt % pseudocumene.

* * * * *